US005997269A

United States Patent [19]
Feitelson

[11] Patent Number: 5,997,269
[45] Date of Patent: Dec. 7, 1999

[54] MEANS FOR DISCOVERING MICROBES

[75] Inventor: Jerald S. Feitelson, San Diego, Calif.

[73] Assignee: Mycogen Corporation, San Diego, Calif.

[21] Appl. No.: 09/098,917

[22] Filed: Jun. 17, 1998

Related U.S. Application Data

[60] Provisional application No. 60/050,374, Jun. 20, 1997.

[51] Int. Cl.$^6$ .............................. C12Q 1/04; C12Q 1/00; C12Q 1/68
[52] U.S. Cl. .................................... 425/34; 435/4; 435/6; 435/252.31; 435/252.5; 435/832; 435/834; 530/300; 536/23.1; 536/23.71
[58] Field of Search ........................ 435/34, 4, 6, 252.31, 435/252.5, 832, 834; 530/300; 536/23.1, 23.71

[56] References Cited

U.S. PATENT DOCUMENTS

| | | |
|---|---|---|
| 4,948,734 | 8/1990 | Edwards et al. . |
| 5,270,448 | 12/1993 | Payne . |
| 5,651,965 | 7/1997 | Payne . |

FOREIGN PATENT DOCUMENTS

| | | |
|---|---|---|
| 9712980 | 4/1997 | WIPO . |
| 9717432 | 5/1997 | WIPO . |

OTHER PUBLICATIONS

Gaertner, F.H., L. Kim (1988) "Current Applied Recombinant DNA Projects" TIBTECH 6(4):S4–S7.

Gaertner, F.H. (1989) "Cellular Delivery Systems for Insecticidial Proteins: Living and Non–Living Microorganisms," in *Controlled Delivery of Crop Protection Agents,* R.M. Wilkins, ed., Taylor and Francis, New York and London, 1990, pp. 245–255.

Couch, T.L. (1980) "Mosquito Pathogenicity of *Bacillus thuringiensis* var. *israelensis*" *Developments in Industrial Microbiology* 22:61–76.

Beegle, C.C. (1978) "Use of Entomogenous Bacteria in Agroecosystems," *Developments in Industrial Microbiology* 20:97–104.

Krieg, A., A.M. Huger, G.A. Langenbruch, W. Schnetter (1983) *Z. Ang. Ent.* 96:500–508.

Hofte, H., H.R. Whiteley (1989) *Microbiological Reviews* 52(2):242–255.

Feitelson, J.S., J. Payne, L. Kim (1992) *Bio/Technology* 10:271–275.

Yamanaka, Satoshi, Akiko Hagiwara, Yukimasa Nishimura, Hiroshi Tanabe, Nobuyoshi Ishibashi (1992) "Biochemical and Physiological Characteristics of Xenorhabdus Species, Symbiotically Associated with Entomopathogenicity Against *Spodoptera litura* (Lepidoptera: Noctuidae)" Arch. Microbiol. 158(6):387–393 **Absract No. XP 002048914.

*Primary Examiner*—Louise N. Leary
*Attorney, Agent, or Firm*—Saliwanchik, Lloyd & Saliwanchik

[57] ABSTRACT

The subject invention concerns a means for discovery of microbes having useful activities. More specifically, the subject invention comprises the use of nematodes as the starting material for discovering novel strains of microbes such as *Bacillus thuringiensis* or other Bacilli. The nematodes are processed by Bacillus isolation techniques to recover the microbes.

25 Claims, No Drawings

MEANS FOR DISCOVERING MICROBES

CROSS-REFERENCE TO A RELATED APPLICATION

This application claims priority from U.S. provisional application Ser. No. 60/050,374, filed Jun. 20, 1997.

BACKGROUND OF THE INVENTION

The soil microbe *Bacillus thuringiensis* (*B.t.*) is a Gram-positive, spore-forming bacterium characterized by parasporal crystalline protein inclusions. These inclusions often appear microscopically as distinctively shaped crystals. The proteins can be highly toxic to pests and specific in their toxic activity. Certain *B.t.* toxin gcenes have been isolated and sequenced, and recombinant DNA-based *B.t.* products have been produced and approved for use. In addition, with the use of genetic engineering techniques, new approaches for delivering these *B.t.* endotoxins to agricultural environments are under development, including the use of plants genetically engineered with endotoxin genes for insect resistance and the use of stabilized intact microbial cells as *B.t.* endotoxin delivery vehicles (Gaertner, F. H., L. Kim [1988] TIBTECH6:S4–S7). Thus, isolated *B.t.* endotoxin genes are becoming commercially valuable.

Until the last ten years, commercial use of *B.t.* pesticides has been largely restricted to a narrow range of lepidopteran (caterpillar) pests. Preparations of the spores and crystals of *B. thuringiensis* subsp. *kurstaki* have been used for many years as commercial insecticides for lepidopteran pests. For example, *B. thuringiensis* var. *kurstaki* HD-1 produces a crystalline δ-endotoxin which is toxic to the larvae of a number of lepidopteran insects.

In recent years, however, investigators have discovered *B.t.* pesticides with specificities for a much broader range of pests. For example, other species of *B.t.*, namely *israelensis* and *morrisoni* (a.k.a. *tenebrionis*, a.k.a. *B.t.* M-7), have been used commercially to control insects of the orders Diptera and Coleoptera, respectively. See Gaertner, F. H. (1989) "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245–255; see also Couch, T. L. (1980) "Mosquito Pathogenicity of *Bacillus thuringiensis* var. *israelensis*," Developments in Industrial Microbiology 22:61–76; Beegle, C. C., (1978) "Use of Entomogenous Bacteria in Agroecosystems," *Developments in Industrial Microbiology* 20:97–104. Krieg et al (Krieg, A., A. M. Huger, G. A. Langenbruch, W. Schnetter(1983)Z. ang. Ent. 96:500–508) describe *Bacillus thuringiensis* var. *tenebrionis*, which is active against two beetles in the order Coleoptera. These are the Colorado potato beetle, *Leptinotarsadecemlineata*, and *Agelastica alni*.

Recently, new subspecies of *B.t.* have been identified, and genes responsible for active δ-endotoxin proteins have been isolated (Höfte, H., H. R. Whiteley (1989) *Microbiological Reviews* 52(2):242–255). Höfte and Whiteley classified *B.t.* crystal protein genes into four major classes. The classes were CryIII (Lepidoptera-specific), CryII (Lepidoptera- and Diptera-specific), CryIII (Coleoptera-specific), and CryIV (Diptera-specific). The discovery of strains specifically toxic to other pests has been reported. (Feitelson. J. S., J. Payne, L. Kim [1992] *Bio/Technology* 10:271–275). CryV has been proposed to designate a class of toxin genes that are nematode-specific.

Regular use of chemical control of unwanted organisms can select for chemical resistant strains. Chemical resistance occurs in many species of economically important insects and has also occurred in nematodes of sheep, goats, and horses. The development of chemical resistance necessitates a continuing search for new control agents having different modes of action.

Xenorhabdus spp. are a commercially significant group of pathogenic bacteria which can infect a variety of insect larvae via a nematode vector host. These bacteria exist in a symbiotic relationship with pathogenic nematodes of the genus Neoaplectana. Steinernema, and Heterorhabditis. This system provides some advantages for the biological control of insect pests because, unlike many other biocontrol agents (such as *Bacillus thuringiensis*), the nematode actively seeks out prey larvae.

Xenorhabdus spp. are Gram negative, facultatively anaerobic, rod shaped bacteria currently assigned to the family Enterobacteriaceae. Two species (*X. nematophilus* and *X. luminescens*) and four subspecies of *X. nematophilus* (*nematophilus, bovienii, poinarii*, and *beddingii*) have been described.

Xenorhabdus spp. are carried in the closed intestine of third instar, infective, juvenile nematodes such as Heterorhabditis. Heterorhabditis spp. possess a specialized, anterior tooth that allows those nematodes to scrape and rupture the hard, exterior cuticle of the insect in order to gain access to the haemocoel. Neoaplectana and Steinernema spp. possess high hydrostatic heads and have an extremely narrow diameter of their anterior region, which enables these nematodes to punch through the softer internal parts of the insect. Once entry to the haemocoel has been gained, these nematodes secrete toxin which inhibits the insect inducible immune system and release their insect-pathogenic bacterial symbiont, thus killing the host insect.

The degree of infectivity of each nematode species/strain for different hosts varies considerably. No one species/strain is most infective for a wide variety of insect hosts. In addition, each genus of nematode hosts a particular species of bacterium. In nematodes of the Heterorhabditis genus, the symbiotic bacterium is *Photorhabdus luminescens*. The interaction between the bacterium Xenorhabdus and the host nematode is also specific. Apparently, *X. nematophilus* are symbiotic with *Steinernematidae* and *X. luminescens* with Heterorhabditidea. *X. nematophilus* isolated from infective nematodes are able to be carried by only a small proportion of other nematodes. Reasons for this specificity are not completely understood, but this might be related to the production of bacterial cell surface components (e.g. fimbriae).

An insecticidal toxin from *Photorhabdus luminescens* that has activity only when injected into Lepidopteran and Coleopteran insect larvae is known. WO 97/17432 (Ensign et al.) reports that proteins from the genus Photorhabdus are orally toxic to insects upon exposure. As reported therein, *Photorhabdus luminescens* (formerly *Xenorhabdus luminescens*) were found in mammalian clinical samples and as a bacterial symbiont of entomopathogenic nematodes of the genus Heterorhabditis.

Although the foregoing was known in the art, the utility of nematodes as a source for other insecticidal bacteria (preferably Gram positive bacteria, preferably bacteria of the genus Bacillus, and preferably species of *Bacillus thuringiensis*) was not previously known. While the art taught of the existence of particular, symbiotic nematodes and certain bacteria as discussed above, the art did not teach or suggest that nematodes could be used as an excellent source for isolating very unique strains of other types of insecticidal bacteria, particularly unique strains of *Bacillus thuringiensis*.

BRIEF SUMMARY OF THE INVENTION

The subject invention pertains to methods for isolating microbes having useful properties. These microbes are preferably Gram-positive bacteria. Bacillus bacteria are preferred. In a preferred embodiment, the subject invention concerns unique and advantageous methods for discovering novel strains of *Bacillus thuringiensis* (*B.t.*). More specifically, the subject invention provides methods whereby nematodes isolated from, for example, soil, plants, animals, or water, are used as the source to obtain novel *B.t.* or other Bacillus strains. Since nematodes are prevalent throughout the environment, the gathering of them can be readily done. The nematodes can be novel or known. Preferably, the nematodes are isolated from the soil and plant sources. Most preferably the source is soil.

*B.t.* or other Bacillus microbes associated with the nematodes are readily isolated, purified, and processed to determine their characteristics using well-known Bacillus isolation techniques in combination with the teachings provided herein.

The subject invention relates to the surprising discovery that nematodes can be used as an excellent source for obtaining very unique bacteria having useful insecticidal properties. The invention process provides new microbes, such as *B.t.* or other Bacilli, useful to serve as biological pesticides, as well as genes and toxins that are responsible for the insecticidal activity.

DETAILED DISCLOSURE OF THE INVENTION

The subject invention provides novel methods for discovering microbes with useful properties. In a preferred embodiment, these microbes are Bacillus bacteria. In a particularly preferred embodiment, these microbes are *Bacillus thuringiensis* which can be used to control pests. More specifically, the invention process uses nematodes as a novel source for isolating *B.t.* microbes. In a preferred embodiment, the nematodes are obtained from soil and/or plant sources. However, the source of the nematodes is not limited to these areas. Rather, any nematode can be processed to identify the presence of *B.t.* microbes.

The isolation and characterization of *B.t.* or other Bacillus microbes obtained from nematodes can be done by using standard, well-known methods in the art in conjunction with the teachings provided herein.

In a specific embodiment, the method of the subject invention can be used to obtain *B.t.* or other Bacillus strains from soil samples. Nematodes can be freshly isolated from samples of various soils and plant cuttings using, for example, the Baermann filter extraction technique. This and other methods for efficiently extracting nematodes from soil or plant tissues are described in the well-illustratedand detailed manual by S. Ayoub entitled, "Plant Nematology: An Agricultural Training Aid" (1980), published by the California Department of Food and Agriculture. Pasteurization can be used for the efficient recovery of *B.t.* spores from the freshly extracted nematodes. Microscopic examination of single colonies growing on sporulation agar can then be used to identify for *B.t.* or other Bacillus strains found in association with soil nematodes.

Those skilled in the art having the benefit of the teachings provided herein will appreciate that alternate methods are available for isolating nematodes from samples such as soil samples. For example, the combined sieving and sucrose flotation can be used to extract nematodes from soil samples.

The methods of the subject invention can, advantageously, be used to isolate *B.t.* or other Bacillus microbes having great diversity in biological characteristics including pesticidal activity. The diversity observed in the *B.t.* isolates which are obtained using the methods of the subject invention include diversity in the crystal morphology of the δ-endotoxins of the *B.t.* isolates. Diversity is also observed in the molecular weight profiles of the toxin proteins.

In a preferred embodiment the bacteria are obtained from living nematodes. It has been found that in accordance with the teachings of the subject invention, these nematodes have a high number of *B.t.* and/or other Bacillus strains associated with them.

The *B.t.* (or other Bacillus strains), and the toxins and genes which can be obtained therefrom, which are isolated according to the subject invention, can be used to control pests by employing standard procedures well known to those skilled in the art. These procedures include applying microbes and/or toxins directly to the pests. The microbes may be the *B.t.* or other Bacillus strains themselves, or recombinant microbes which express *B.t.* or other Bacillus toxins. Also, plants may be transformed by polynucleotide sequences which express *B.t.* or other Bacillus toxins. These teachings are well known and readily practiced by those skilled in the art and are disclosed in, for example, WO 97/12980.

It should be understood that the examples and embodiments described herein are for illustrative purposes only and that various modifications or changes in light thereof will be suggested to persons skilled in the art and are to be included within the spirit and purview of this application and the scope of the appended claims.

I claim:

1. A method for identifying a novel, pesticidal microorganism; wherein said microorganism is other than a microorganism of a genus selected from the group consisting of Photorhabdus and Xenorhabdus; wherein said method comprises isolating a microbe from a nematode, and characterizing said microorganism to determine if said microbe is a novel microorganism.

2. The method, according to claim 1, wherein said method further comprises the step of assaying said microbe for pesticidal activity.

3. The method, according to claim 1, wherein the characterizing step comprises determining if said microbe expresses a novel toxin.

4. The method, according to claim 1, wherein the characterizing step comprises determining if said microbe comprises a novel gene encoding a pesticidal toxin.

5. The method, according to claim 1, wherein said microbe is a bacterium.

6. The method, according to claim 5, wherein said bacterium is a Gram-positive bacterium.

7. The method, according to claim 5, wherein said bacterium is a Bacillus.

8. The method, according to claim 7, wherein said Bacillus is a *Bacillus thuringiensis*.

9. The method, according to claim 7, wherein said Bacillus is a *Bacillus cereus*.

10. The method, according to claim 8, wherein said nematode is a soil nematode.

11. The method, according to claim 1, wherein said nematode is a plant nematode.

12. The method, according to claim 1, wherein said nematode is a water nematode.

13. The method, according to claim 1, wherein said nematode is an animal nematode.

14. The method, according to claim 1, wherein said nematode is a living nematode.

15. A novel microorganism obtained by the process of claim 1.

16. The microorganism, according to claim 15, wherein said microorganism is a Gram-positive bacterium.

17. The microorganism, according to claim 15, wherein said microorganism is a Bacillus.

18. The microorganism, according to claim 15, wherein said microorganism is a *Bacillus thuringiensis*.

19. The microorganism, according to claim 15, wherein said microorganism is a *Bacillus cereus*.

20. The microorganism, according to claim 15, wherein said microorganism is toxic to western corn rootworm.

21. The microorganism, according to claim 15, wherein said microorganism is toxic to nematodes.

22. A novel toxin obtained from the microorganism of claim 15.

23. A novel toxin gene obtained fron the microorganism of claim 15.

24. The method according to claim 1, wherein said microorganism is active against a pest other than a nematode.

25. The method according to claim 1, wherein said microorganism is not active against nematode.

* * * * *

UNITED STATES PATENT AND TRADEMARK OFFICE
CERTIFICATE OF CORRECTION

PATENT NO.   : 5,997,269
DATED        : December 7, 1999
INVENTOR(S)  : Jerald S. Feitelson Page 1 of 1

It is certified that error appears in the above-identified patent and that said Letters Patent is hereby corrected as shown below:

Column 1,
Line 14: "gcenes" should read -- genes --.
Line 59: "CryIII" should read -- CryI --.

Column 4,
Line 58: "according to claim 8," should read -- according to claim 1, --.

Signed and Sealed this

Twenty-eighth Day of August, 2001

Attest:

NICHOLAS P. GODICI
Attesting Officer  Acting Director of the United States Patent and Trademark Office